(12) United States Patent
Schlomka et al.

(10) Patent No.: US 7,474,728 B2
(45) Date of Patent: Jan. 6, 2009

(54) COMPUTED TOMOGRAPHY APPARATUS

(75) Inventors: Jens-Peter Schlomka, Hamburg (DE); Geoffrey Harding, Hamburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 10/518,848

(22) PCT Filed: Jun. 19, 2003

(86) PCT No.: PCT/IB03/02904

§ 371 (c)(1),
(2), (4) Date: Mar. 15, 2006

(87) PCT Pub. No.: WO2004/002316

PCT Pub. Date: Jan. 8, 2004

(65) Prior Publication Data

US 2006/0171502 A1    Aug. 3, 2006

(30) Foreign Application Priority Data

Jun. 28, 2002 (DE) ................. 102 28 941

(51) Int. Cl.
  *G01N 23/00* (2006.01)
  *G01N 23/201* (2006.01)
(52) U.S. Cl. .................. 378/6; 378/7; 378/86
(58) Field of Classification Search .......... 378/4, 378/7, 19, 37, 70, 86–90, 145–150
See application file for complete search history.

(56) References Cited

U.S. PATENT DOCUMENTS 2,549,987 A    4/1951   Parrish et al.
5,164,976 A  * 11/1992  Scheid et al. ............. 378/146
6,175,117 B1 *  1/2001  Komardin et al. ....... 250/363.06
6,483,891 B1 * 11/2002  Lazarev et al. ............. 378/37
2006/0140340 A1 *  6/2006  Kravis ....................... 378/57

FOREIGN PATENT DOCUMENTS

DE      10127267 A1      12/2002
EP       1062914 A1      12/2000
WO   PCT/US98/09094   *  5/1998
WO        9849939 A1    11/1998

OTHER PUBLICATIONS

Stonestrom, J. P., et al.; Scatter Considerations in Fan Beam Computerized Tomographic Systems; 1976; IEEE Trans. on Nuclear Science; 23(5)1453-1458.

* cited by examiner

*Primary Examiner*—Irakli Kiknadze
(74) *Attorney, Agent, or Firm*—Michael E. Belk

(57) ABSTRACT

The invention relates to a computed tomography apparatus (CT apparatus) for imaging by means of radiation having traversed an object to be examined (that is, directly transmitted radiation), as well as by means of radiation scattered by the object to be examined, which apparatus includes a radiation source (S), a detector arrangement (16) and a device whereby the radiation (41*a*) having traversed the object to be examined can be blocked at least to an extent that the intensity incident on the detector arrangement (16) does not substantially exceed the intensity of radiation (41*b*) scattered by the object (13) to be examined and incident on the detector arrangement (16). The invention enables the detection of scattered radiation (CSCT mode) which is not affected by crosstalk from the transmitted radiation, even when the detector arrangement does not satisfy severe requirements as regards crosstalk properties and/or is configured as a single-row detector arrangement.

20 Claims, 2 Drawing Sheets

COMPUTED TOMOGRAPHY APPARATUS

The invention relates to a computed tomography apparatus (CT apparatus) for imaging by means of radiation having traversed an object to be examined (that is, directly transmitted radiation), as well as by means of radiation scattered by the object to be examined.

A CT apparatus of this kind is known, for example, from EP 1 127 546. It comprises essentially a radiation source for generating a fan beam which traverses an object to be examined, as well as a two-dimensional detector arrangement which consists of a plurality of individual detector elements which are arranged in rows and columns in conformity with the length and the width, respectively, of the cross-section of the fan beam. The number of columns generally is substantially larger than the number of rows and the longitudinal dimension of the detector arrangement is substantially larger than its dimension in the direction of the width of the cross-section of the fan beam.

The angle of aperture of the fan beam in the direction of its width (that is, in the direction perpendicular to the fan plane) can be varied by means of diaphragm devices. When the radiation having traversed the object to be examined (the transmitted radiation) is to be detected as well as the radiation scattered by the object, such a diaphragm device is selected that a comparatively small width of the fan beam is obtained. In that case the directly transmitted radiation is detected essentially by the central row of the detector arrangement, whereas the scattered radiation, being directed away from the plane of the fan beam to both sides, is incident on the outer rows of the detector arrangement.

In order to optimize the pulse momentum transfer spectrum, furthermore, a collimator arrangement which consists of a plurality of lamellas is arranged between the object to be examined and the detector arrangement, which lamellas subdivide the fan beam into a number of segments so that the detector elements that are situated in one column are struck by transmitted and scattered radiation from the same segment of the object to be examined.

However, it has been found that the detection of the scattered radiation by means of in particular those detector rows which adjoin the central row (rows) is disturbed by crosstalk due to the incidence of the transmitted radiation which is significantly more intense for given objects to be examined. This problem may become more serious notably when use is made of detector arrangements having a comparatively small width such as included in some known CT apparatus.

If, moreover, single-row detector arrangements are used, generally speaking, detection of the scattered radiation is even impossible by means of such CT apparatus.

Therefore, it is an object of the invention to provide a CT apparatus of the kind set forth whereby the radiation scattered by an object to be examined can be detected at least substantially without being affected by radiation having traversed the object to be examined (that is, transmitted radiation).

It is also an object of the invention to provide a CT apparatus whereby the radiation scattered by an object to be examined can be detected at least substantially without being affected by radiation having traversed the object, that is, even when use is made of a detector arrangement comprising only one detector row or only a few detector rows.

Finally, it is also an object of the invention to provide a CT apparatus whereby transmitted and scattered radiation (CT and CSCT mode) can be detected simultaneously when use is made of a multi-row detector arrangement, without the measurement of the scattered radiation being significantly affected by crosstalk from the transmitted radiation.

In conformity with claim 1 the object is achieved by means of a computed tomography apparatus which includes a radiation source, a detector arrangement and a device with which (transmitted) radiation having traversed an object to be examined can be stopped at least to such an extent that its intensity which is incident on the detector arrangement does not significantly exceed the intensity of radiation scattered by the object to be examined and incident on the detector arrangement.

It has been found that the required degree of stopping is dependent essentially on the quality of the detector arrangement and notably on the crosstalk attenuation thereof as well as on the desired image quality. The less the crosstalk between neighboring detector elements or detector rows and the lower the requirements imposed on the image quality, the lower the adjusted degree of said stopping may be.

A special advantage of this solution resides in the fact that the simultaneous detection of transmitted and scattered radiation can also be carried out by means of detector arrangements which do not satisfy severe requirements in respect of their crosstalk properties, so that additionally costs can be saved.

It is to be noted that U.S. Pat. No. 6,175,117 discloses a tissue analysis device which includes a beam-forming device for the analysis of substances in the breast as well as a detector for the detection of radiation transmitted and scattered by the breast, a filter which comprises a number of areas which are transparent to radiation and absorb the radiation being arranged in front of the filter. Apart from the fact that this device is not a computed tomography apparatus, this filter structure is provided for a detector arrangement which has a comparatively large surface area which cannot solve the problem to be solved in accordance with the invention, so that the cited publication is not considered to be of relevance.

The dependent claims relate to advantageous further embodiments of the invention.

The embodiments in conformity with the claims 2 and 7 offer the advantage that the transmitted and the scattered radiation can also be detected simultaneously when the detector arrangement is suitably proportioned.

The embodiment in conformity with claim 3 represents a particularly economical solution.

The embodiments disclosed in the claims 4 and 6 can also be implemented at a later stage, while using limited means only, in already existing computed tomography apparatus.

The embodiments disclosed in the claims 5 and 9 enable measurement of the scattered radiation at different angles relative to an object to be examined.

Further details, features and advantages of the invention will become apparent from the following description of preferred embodiments which is given with reference to the drawing. Therein:

Figure 1:
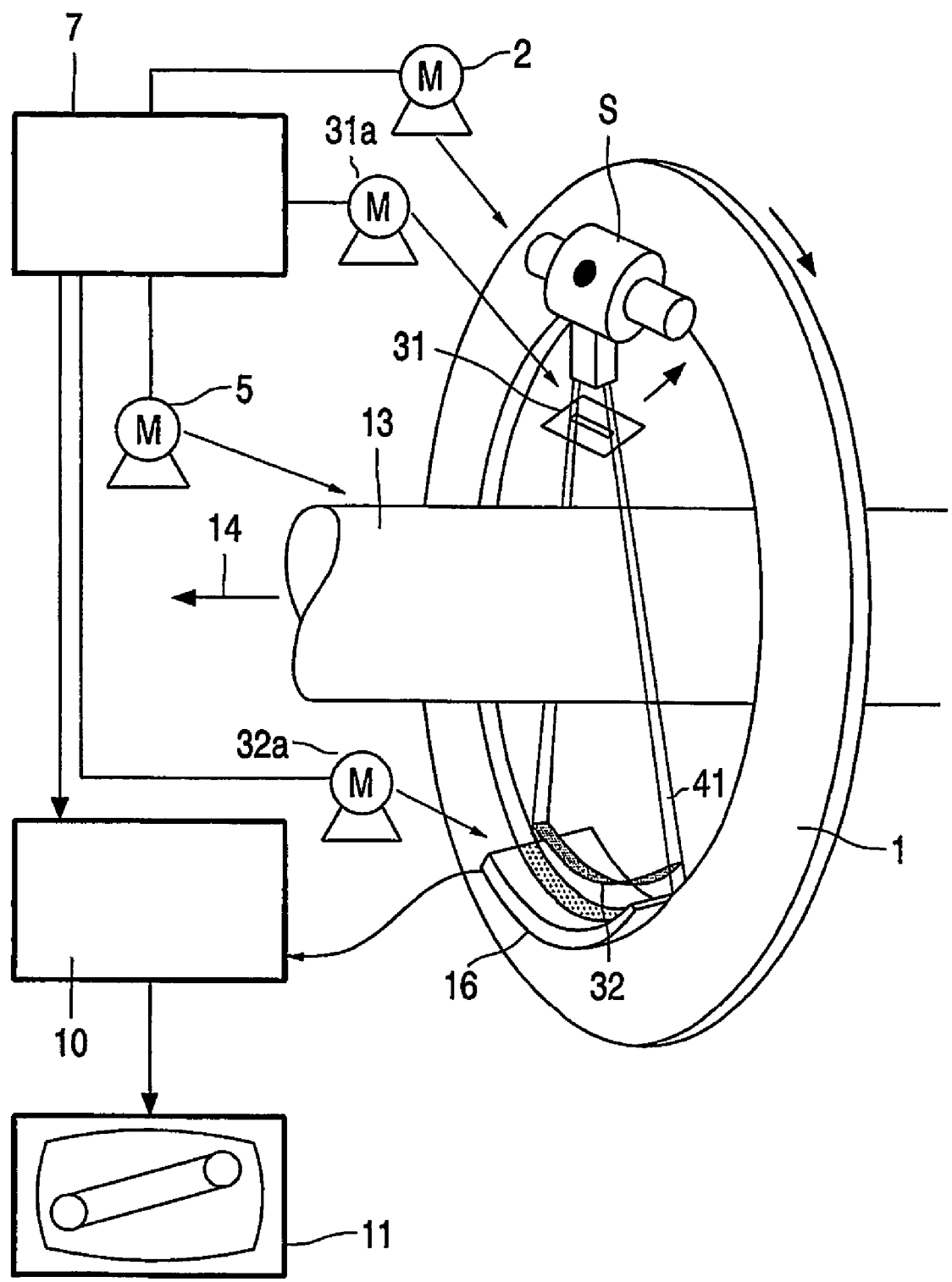
FIG. 1 shows diagrammatically the essential components of a CT apparatus in accordance with the invention.

FIG. 1 is a diagrammatic representation of the essential components of a CT apparatus in accordance with the invention. The apparatus includes a gantry 1 which can be rotated about an axis of rotation 14 by means of a first motor 2. On the circumference of the gantry 1 there is mounted a radiation source S, for example, an X-ray source, which includes a first collimator 31 whereby a radiation beam 41 (primary radiation) can be generated. After said radiation beam 41 has traversed the examination zone in which an object 13 to be examined is situated and/or after it has been scattered therein, it is incident on a second collimator 32 as well as on a detector arrangement 16.

The detector arrangement 16 is composed of a plurality of detector elements which are arranged in the form of a matrix which comprises at least one row and a plurality of columns. The detector rows extend in the circumferential direction of the gantry 1 whereas the columns extend perpendicularly thereto. The detector arrangement 16 and the second collimator 32 are also attached to the gantry 1.

The object 13 to be examined can be displaced in the direction of the axis of rotation 14 of the gantry by means of a second motor 5.

Using a first drive unit 31a, the first collimator 31 or the radiation source S can be displaced in a direction perpendicular to the plane of the gantry 1. Alternatively or additionally, there is provided a second drive unit 32a whereby the second collimator 32 and the detector arrangement 16 can also be displaced in a direction perpendicular to the plane of the gantry 1.

A control unit 7 is provided for controlling the motors 2, 5 and the drive units 31a, 32a, said control unit itself being connected to an image processing computer 10. The detector arrangement 16 is also connected to the computer 10 which processes the detector signals and forms an image of the object 13 to be examined on a monitor 11.

As is also shown in FIG. 1, the radiation source S and the first collimator 31 produce a fan-shaped radiation beam 41 (fan beam). The angle of aperture of the fan beam in the plane of the gantry 1 and the length of the detector arrangement 16 in the circumferential direction of the gantry 1 are preferably adapted to one another in such a manner that the entire length of the detector arrangement 16 can be exposed. The width of the fan beam in the direction perpendicular to the fan plane defined by the angle of aperture, however, is substantially smaller and preferably proportioned to be such that it covers only one detector row or only a few detector rows of the detector arrangement 16.

Alternatively, the radiation source S and the collimator 31 may also be proportioned in such a manner that a conical radiation beam is generated.

In order to optimize the pulse momentum transfer spectrum it is again possible to arrange, as described in the cited EP 1 127 546, a collimator arrangement in the form of a plurality of lamellas between the object 13 to be examined and the detector arrangement 16, which lamellas subdivide the radiation beam 41 into a number of segments in such a manner that the detector elements present in one column are struck by transmitted and scattered radiation from the same segment of the object 13 to be examined. Therefore, the publication EP 1 127 546 is incorporated in this description by way of reference.

Figures 2, 3, 4:
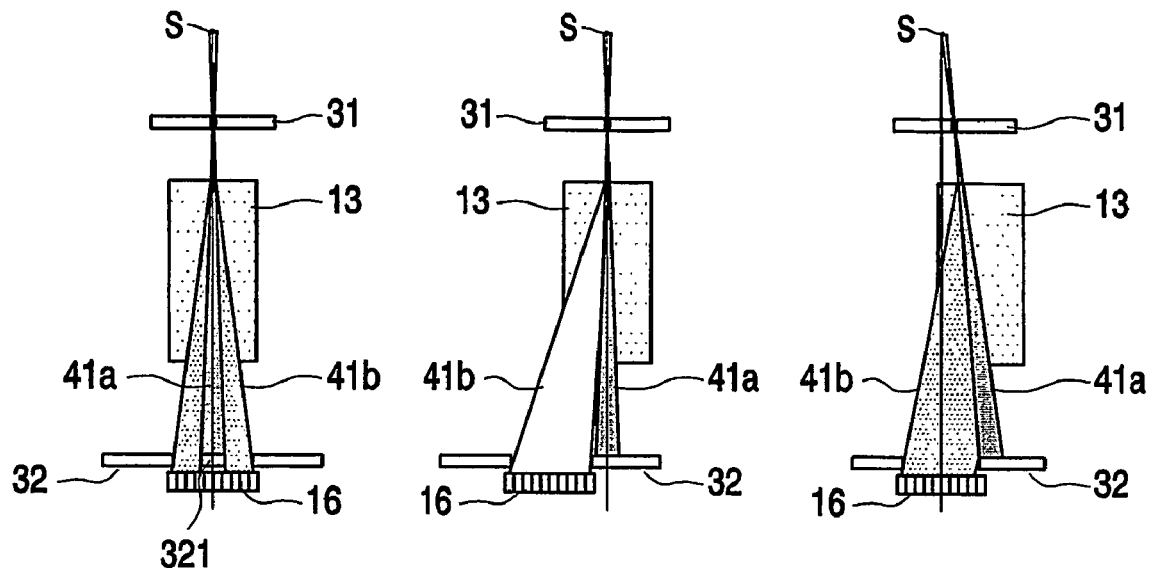
FIG. 2 shows a first embodiment of the invention.
FIG. 3 shows a second embodiment of the invention.
FIG. 4 shows a third embodiment of the invention.

The FIGS. 2 to 4 are side elevations taken in a direction parallel to the plane of the gantry 1 (that is, essentially also parallel to the plane of the fan beam 41. These Figures diagrammatically show the radiation source S, the first collimator 31, the object 13 to be examined, the second collimator 32 as well as the detector arrangement 16.

As can also be seen in FIG. 2, in the first embodiment of the invention the (transmitted) radiation 41a having traversed the object 13 to be examined is completely stopped by a central region 321 of the second collimator 32, so that it is no longer incident on the detector arrangement 16. The radiation 41b scattered by the object 13 to be examined, however, can reach the detector arrangement 16 without being obstructed, that is, via openings in the second collimator 32 which are situated laterally of the central region 321.

In the second embodiment as shown in FIG. 3 this object is achieved thanks to the fact that the detector arrangement 16 and the second collimator 32 (in as far as necessary) have been shifted laterally with respect to the (central) position shown in FIG. 2, that is, in a direction perpendicular to the plane of the gantry 1 and hence to the plane of the fan beam 41; they have been shifted to such an extent that the transmitted radiation 41a is directed so as to bypass the detector arrangement 16 and/or is incident on a region of the second collimator 32 which is not transparent to this radiation. The scattered radiation 41b emanating from the object 13 to be examined is incident on the detector arrangement 16 via an appropriate opening in the second collimator 32. The shift of the second collimator 32 and the detector arrangement 16 can be realized in steps, by way of the control unit 7 and the second drive unit 32a, in order to detect and evaluate scattered radiation 41b with different scatter angles.

In the embodiment shown in FIG. 4, however, the first collimator 31 is shifted relative to the (central) position shown in the FIGS. 2 and 3 in a direction perpendicular to the plane of the gantry 1, whereas the second collimator 32 and the detector arrangement 16 remain in the position shown in FIG. 2, so that the transmitted radiation 41a traverses the object 13 to be examined at an angle relative to the plane of the gantry 1 and hence is not directed onto the detector arrangement 16. The scattered radiation 41b, however, is again incident on the detector arrangement 16 via an appropriate opening in the second collimator 32. In order to detect and evaluate scattered radiation 41b with different scatter angles, the first collimator 31 can again be displaced in steps in said direction by way of the control unit 7 and the first drive unit 31a. Alternatively, instead of displacing the first collimator 31, the radiation source S can be displaced in the opposite direction.

The above three embodiments enable unobstructed detection and evaluation of the scattered radiation 41b by means of a single-row detector arrangement as well as by means of a multi-row detector arrangement 16.

The principles illustrated in the FIGS. 2 to 4, in conformity with which the transmitted radiation 41a is blocked and only the scattered radiation 41b is directed onto the detector arrangement 16, can also be reversed if necessary, that is, in such a manner that the scattered radiation 41b is blocked at least substantially and the transmitted radiation 41a is incident on the detector arrangement 16.

Figures 5, 6:
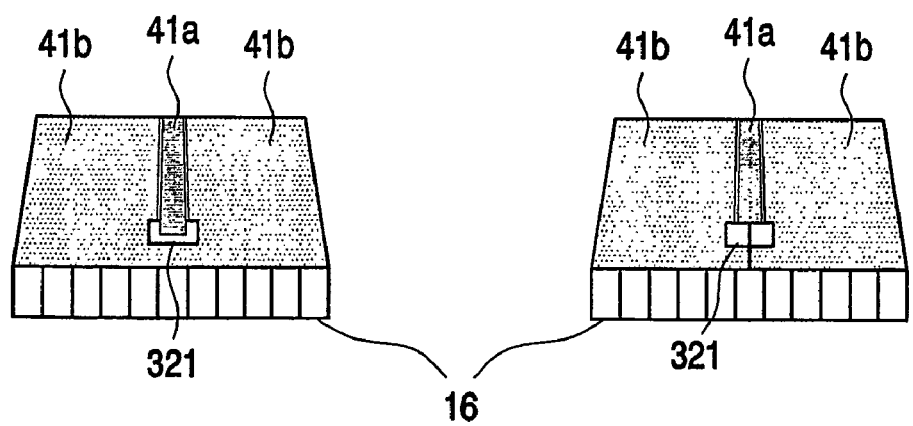
FIG. 5 shows a fourth embodiment of the invention.
FIG. 6 shows a fifth embodiment of the invention.

However, if the transmitted radiation and the scattered radiation are to be detected simultaneously, preferably the first embodiment as shown in FIG. 2 is modified in conformity with FIG. 5 or FIG. 6.

The FIGS. 5 and 6 are side elevations, at an enlarged scale relative to FIG. 2, of a part of a detector arrangement 16 which comprises a plurality of detector rows which extend in a direction parallel to the plane of the fan beam 41.

As opposed to the first embodiment as shown in FIG. 2, in the fourth and the fifth embodiment as shown in the FIGS. 5 and 6 the central region 321 of the second collimator 32 does not completely block the transmitted radiation 41a, but partly lets this radiation through so that its intensity is only so high that the detection of the scattered radiation 41b is not influenced or disturbed by crosstalk from the transmitted radiation 41 in neighboring detector rows.

To this end, the central region 321 of the second collimator 32 contains a material of an appropriate thickness which absorbs the radiation in the fourth embodiment as shown in FIG. 5.

In the fifth embodiment as shown in FIG. 6 the central region 321 of the second collimator 32 is provided with an opening in the form of a narrow gap or slit wherethrough only a part of the radiation can pass.

For the proportioning of the absorptivity of the central region 321 or the width and length of the opening in this region 321 the fact must be taken into account that, in dependence on the object density, the intensity of the transmitted radiation 41a may be a factor of from 10 to 1000 higher than the intensity of the scattered radiation 41b. The attenuation of the transmitted radiation intensity should preferably also be of this order of magnitude, so that the transmitted radiation 41a and the scattered radiation 41b are incident on the detector arrangement 16 with approximately the same intensity.

If necessary, of course, this principle can also be reversed when the central region 321 is arranged in the path of the scattered radiation in order to attenuate the scattered radiation 41b relative to the transmitted radiation 41a for some reason.

A special advantage of the invention resides in the fact that it enables switching over between the imaging and evaluation on the basis of the transmitted radiation (CT mode) and the imaging and evaluation on the basis of the coherent scattered radiation (CSCT mode) during the examination of an object. Significantly better examination results can thus be achieved. This holds for diagnoses in the medical field as well as for the examination of materials.

The invention claimed is:

1. A computed tomography apparatus which includes;
   a radiation source that emits radiation that traverses an examination zone, wherein the radiation source rotates around the examination zone along a longitudinal axis;
   a detector arrangement that detects radiation that traverses the examination zone, wherein the detector arrangement is configured for displacement, with respect to the radiation source, in a direction along the longitudinal axis;
   a first drive unit configured to displace the detector arrangement along the longitudinal axis so that substantially all transmission radiation that traverses the examination zone bypasses the detector arrangement and scattered radiation that traverses the examination zone illuminates the detector arrangement.

2. A computed tomography apparatus as claimed in claim 1, in which the radiation source is arranged to form an essentially fan-shaped radiation beam and the detector arrangement comprises a plurality of detector elements which are arranged in rows and columns in conformity with the length and the width, respectively, of the cross-section of the radiation beam in the detector plane.

3. The computed tomography apparatus as claimed in claim 1, in which the detector arrangement comprises a plurality of detector elements which are arranged in a row.

4. The computed tomography apparatus as claimed in claim 1, further including: a source collimator arranged with respect to the radiation source to be offset from the radiation source in a direction perpendicular to a propagation direction of the radiation beam in such a manner that the transmission radiation traversing the examination zone substantially bypasses the detector arrangement.

5. The computed tomography apparatus as claimed in claim 4, wherein the source collimator is configured for displacement in the direction perpendicular to the propagation direction of the radiation beam, and further including a second drive unit for selectively displacing the source collimator with respect to the radiation source in such a manner that the transmission radiation traversing the examination zone substantially bypasses the detector arrangement.

6. The computed tomography apparatus as claimed in claim 1, further including a detector collimator arranged between the examination zone and the detector arrangement, wherein the detector collimator includes a sub-region that attenuates the transmission radiation so that an intensity of the transmission radiation illuminating the detector arrangement is substantially equal to an intensity of the scattered radiation illuminating the detector arrangement.

7. The computed tomography apparatus as claimed in claim 6, wherein the sub-region includes an opening through which transmission radiation traverses substantially unattenuated and illuminates the detector arrangement.

8. The computed tomography apparatus as claimed in claim 1, wherein the radiation source is configured for displacement along the longitudinal axis, and further including:
   a source collimator; and
   a second drive unit that displaces the radiation source, with respect to the source collimator, along the longitudinal axis so that the transmission radiation traversing the examination zone substantially bypasses the detector arrangement.

9. The computed tomography apparatus as claimed in claim 1, wherein only the scattered radiation illuminates the detector arrangement.

10. A computed tomography apparatus, comprising:
    a radiation source that emits radiation that traverses an examination zone, wherein the radiation source rotates about the examination region along an axis of rotation;
    a detector arrangement that detects radiation that traverses the examination zone; and
    a collimator arranged between the examination zone and the detector arrangement,
    wherein the collimator includes a sub-region that attenuates transmission radiation so that an intensity of the transmission radiation traversing the sub-region and illuminating the detector arrangement is substantially equal to an intensity of scattered radiation illuminating the detector arrangement, and
    wherein the sub-region includes an opening through which transmission radiation traverses substantially unattenuated and illuminates the detector arrangement.

11. The computed tomography apparatus of claim 10, wherein the radiation source is configured to move in a direction along the axis of rotation, and further including:
    a source collimator; and
    a drive unit that selectively displaces the radiation source with respect to the source collimator along the axis of rotation;
    wherein the drive unit displaces the radiation source so that the transmission radiation traversing the examination zone substantially bypasses the detector arrangement.

12. The computed tomography apparatus of claim 10, further including a drive unit that laterally displaces the detector arrangement, with respect to the radiation source, in a direction along the axis of rotation so that substantially all transmission radiation traversing the examination zone bypasses the detector arrangement and scattered radiation traversing the examination zone illuminates the detector arrangement.

13. The computed tomography apparatus of claim 10, further including:
    a source collimator configured to move in a direction along the axis of rotation with respect to the radiation source; and
    a drive unit for selectively displacing the source collimator along the axis of rotation;
    wherein the drive unit selectively displaces the source collimator, with respect to the radiation source, so that the source collimator is offset from the radiation source so that the transmission radiation traversing the examination zone substantially bypasses the detector arrangement.

14. A method, comprising:

selectively directing a radiation beam with respect to a detector arrangement so that transmission radiation, corresponding to the radiation beam, that traverses an examination zone and bypasses the detector arrangement; and detecting scattered radiation, corresponding to the radiation beam, that traverses the examination zone and illuminates the detector arrangement.

15. The method of claim 14, wherein the act of selectively directing the radiation beam includes selectively shifting the detector arrangement in a direction perpendicular to a propagation direction of the radiation beam.

16. The method of claim 14, wherein the act of selectively directing the radiation beam includes selectively shifting a source collimator with respect to a radiation source that emits the radiation beam in a direction perpendicular to a propagation direction of the radiation beam.

17. The method of claim 14, wherein the act of selectively directing the radiation beam includes selectively shifting a radiation source that emits the radiation beam with respect to a source collimator in a direction perpendicular to a propagation direction of the radiation beam.

18. The method of claim 14, wherein the transmission and the scattered radiation are concurrently detected during a same data acquisition cycle.

19. The method of claim 18, further including attenuating the transmission radiation using a device with a thickness configured to attenuate the transmission radiation so that its intensity is about the same as the intensity of the scattered radiation.

20. The method of claim 19, wherein the device includes an opening through which the transmission radiation passes through substantially unattentuaed.

* * * * *